United States Patent [19]

Schäfer et al.

[11] Patent Number: 4,542,739
[45] Date of Patent: Sep. 24, 1985

[54] WOUND TEXTILE

[75] Inventors: Ewald Schäfer, Wolfstein; Harald Jung, Kreimbach-Kaulbach, both of Fed. Rep. of Germany

[73] Assignee: Firma Karl Otto Braun Kg, Fed. Rep. of Germany

[21] Appl. No.: 458,807

[22] Filed: Jan. 18, 1983

[30] Foreign Application Priority Data

Apr. 14, 1982 [DE] Fed. Rep. of Germany ....... 3213673

[51] Int. Cl.⁴ ............................................. A61F 13/00
[52] U.S. Cl. ................................................ 128/156
[58] Field of Search ................ 128/132 D, 155, 156, 128/160, 165–169; 66/169–171, 190–195

[56] References Cited

U.S. PATENT DOCUMENTS

| | | | |
|---|---|---|---|
| 3,709,221 | 1/1973 | Riely | 128/156 |
| 4,161,176 | 7/1979 | Harris | 128/155 |
| 4,173,131 | 11/1979 | Pendergrass | 66/192 |
| 4,203,435 | 5/1980 | Krull et al. | 128/156 |
| 4,205,674 | 6/1980 | Porat et al. | 128/156 |
| 4,215,684 | 8/1980 | Westip | 128/156 |
| 4,236,550 | 12/1980 | Braun | 139/421 |

*Primary Examiner*—John D. Yasko
*Attorney, Agent, or Firm*—Beveridge, DeGrandi & Weilacher

[57] ABSTRACT

An elastic, non-sticking wound textile formed of a highly elastic knitted fabric with a mesh-forming thread of a completely synthetic material facing the wound and highly absorbent yarns incorporated as the weft.

4 Claims, 2 Drawing Figures

WOUND TEXTILE

BACKGROUND OF THE INVENTION

Elastic, non-sticking wound textiles are known from German Pat. No. 1,492,434, DOS Nos. 2,656,041 and 2,656,042. The wound textile is prevented from sticking to the wound mainly by weaving or knitting together varyingly shrinking yarns or threads so that, in the case of secretion, the highly twisted thread or threads are shortened, leading to the formation of a tunnel. Bandaging materials of this type are very suitable for quick-acting wound bandages, but do not have an optimum action when used as compresses for wounds with a high secretion rate, because there can be so much secretion that the textile can no longer completely absorb it. As a result, the wound textile can stick to the wound, which is prejudicial to the healing process.

DAS No. 1,143.299 discloses a two-layer bandaging material, which is woven and inelastic. The absorbent layer of this bandaging material, which is in the form of a hydrophilic fabric, is joined to a second fabric layer made from non-swellable threads or tapes. This bandaging material is a double fabric, which is inelastic and difficult and expensive to manufacture, so that it is virtually unusable as a disposable article as a result of the high manufacturing costs.

German Pat. No. 529,559 discloses a wound bandage in which a thin, flexible metal fabric or gauze layer is placed on a highly absorbent muslin cushion, so that there is only an insignificant reduction in the absorptivity of the latter. As both layers are not firmly joined together during the production of such a wound bandage, a folding process must take place in a separate operation, which makes the manufacturing procedure complicated and costly.

German Pat. No. 820,179 discloses a bandaging material for discharging wounds. This material is constructed in such a way that it has a moisture-impermeable layer on the side remote from the wound, which seals the latter. The joining of the synthetic material to the muslin fabric and the layers of staple fibre cotton wool is brought about by stitched seams. The disadvantage of this bandaging material is that as a result of the construction, particularly the moisture-impermeable layer in the form of a synthetic material, moist warm chambers form, which are conducive to bacterial and mycotic attacks to the wound.

Swiss Pat. No. 193,469 describes a wound bandage formed from a fibrous material and a film material, the latter being cellulose or cellulose derivatives. The perforated film layer must not stick to the wound. The absorbent layer in this bandage consists of a fibrous material layer, which is completely surrounded by the film layer and is firmly joined thereto. It is disadvantageous that through the application of a moisture-impermeable layer, both the absorptivity and the air ventilation characteristics are considerably impaired, so that here again moist, warm chambers can form, which favour bacterial and mycotic attacks to the wound.

In addition, wound compresses are known, which consist of woven or non-woven materials, whose surface is prevented from sticking to the wound by sintering on a synthetic material layer. However, wound compresses formed in this way have a number of disadvantages. As a result of sintering on synthetic materials, the compresses lose their plasticity, so that when forming the compress onto a wound in the vicinity of joints, e.g. the knee, "bag formation" occurs, and as a result pressure points cannot be avoided. A further important disadvantage of such compresses is that particularly in the case of high secretion levels, the internal stability of the non-woven fabric absorbent layer remote from the wound side is lost, because stability only exists between the loose fibres in the dry state. Thus, on absorbing secretion, the individual fibre bundles are loosened and clump together, so that between the covering layer and the absorbent layer an adhesive secretion film is formed, which prevents air ventilation. These disadvantages also occur with wound compresses, whose absorbent layer is made non-sticking by sintering, sticking or melting on a foil.

BRIEF SUMMARY OF THE INVENTION

The problem of the present invention is to provide a highly elastic knitted fabric which, whilst avoiding the disadvantages of known wound textiles, ensures good absorptivity, a good air permeability and a good secretion holding capacity, and at the same time does not stick to the wound.

According to the invention, this problem is solved by a wound textile made from a highly elastic knitted fabric with a mesh-forming thread formed from fully synthetic material, such as polyester, polyamide, polypropylene, etc. facing the wound, and threads made from highly absorbent yarns such as cotton, staple fiber, linen, etc. incorporated as weft threads into the web.

In a wound textile constructed in this way in the layer L1, which forms the mesh, the mesh-forming thread is constituted by a completely synthetic material, such as polyester, polyamide, polypropylene or similar materials. However, layers L2, L3 and L4 are formed of highly absorbent yarns of cotton, staple fibre, linen, etc.

The use of synthetic material yarns or threads means that layer L1 cannot absorb wound secretion due to chemical structure. The wound secretion is sucked through the knitted fabric by the absorbent layer positioned on the back, i.e. the secretion passes through the polyester, polyamide, polypropylene or similar covering layer and is bound in intermicellar manner by the absorbent layer. The polyester, polyamide or polypropylene covering side facing the wound absorbs no secretion during this process and remains absolutely dry, so that no sticking to the wound can take place.

Through the use of one or more twisted or hard wire threads, structures can be formed which have a more or less pronounced tunnel formation and consequently improve the ventilation, i.e. access of air to the wound. This tunnel formation initially takes place in the absorbent layer remote from the wound and the highly twisted individual or twisted crepe threads incorporated into this layer are shortened on access of wound secretion. Due to the tight connection between the absorbent layer and the covering layer, the tunnel formation is directly transferred at all points to the covering layer made from synthetic fibres.

The tight connection between the absorbent and covering layers also leads to a very stable wound, support, which is not sensitive to mechanical damage.

According to a further feature of the invention, for increasing the therapeutic effect of the wound textile, the wound side, i.e. the polyamide, polyester or polypropylene threads, is dyed with a blue, toxicologically unobjectionable dye. As a result of this indication of the wound support side not only is the doctor immediately and rapidly aware of which side is which, but also a temperature reduction of about 2° to 3° C. is achieved in the wound area, so that the thermophysiological behaviour is favourably influenced and bacterial growth significantly reduced.

Due to a more or less pronounced roughening of the wound-remote side, the pore volume of the absorbent layer is increased and consequently the secretion holding capacity improved. Due to the varying degree of roughening, as a function of use, the secretion holding capacity can even be controlled. The rough fleece also leads to a better cushioning effect and consequently a better protection of the wound against external influences, such as e.g. pressure.

A wound textile constructed in this way with its excellent absorptivity, ventilation characteristics and temperature reduction in the wound is far superior to the hitherto known wound textiles.

The wound textile according to the invention has a number of advantages. As a result of its non-sticking wound covering side, high absorptivity and high elasticity, the knitted fabric is able to bind in intermicellar manner large quantities of secretion, without the formation of moist, warm chambers. Due to the high capillarity, i.e. the draining action, the wound is made dry in a very short time, without there being any sticking of the wound textile to the wound. Through the introduction of highly twisted single or twisted crepe threads, ventilation tunnels are formed, even in the case of moisture access, and these further increase air supply to the wound and consequently aid the healing action. As a result of the blue colouring of the wound textile covering layer, a cooling action is exerted on the wound area and bacterial growth is inhibited. Due to the firm connection of the two layers, namely the non-adhering wound support layer and the absorbent layer, a wound bandaging material is obtained, which combines the advantages of all the known, but varying bandaging materials.

To prevent a separation of the wound textile in the running direction of the synthetic thread, the knitted fabric undergoes a powerful heat treatment, so that a fixing of the thermoplastic threads, e.g. of polyester, polyamide, polypropylene, etc. is achieved. This ensures a high-separating strength.

BRIEF DESCRIPTION OF THE DRAWINGS

The invention is described in greater detail hereinafter relative to non-limitative embodiments and the attached drawings, wherein.

DETAILED DESCRIPTION OF THE PREFERRED EMBODIMENTS

Figure 1:
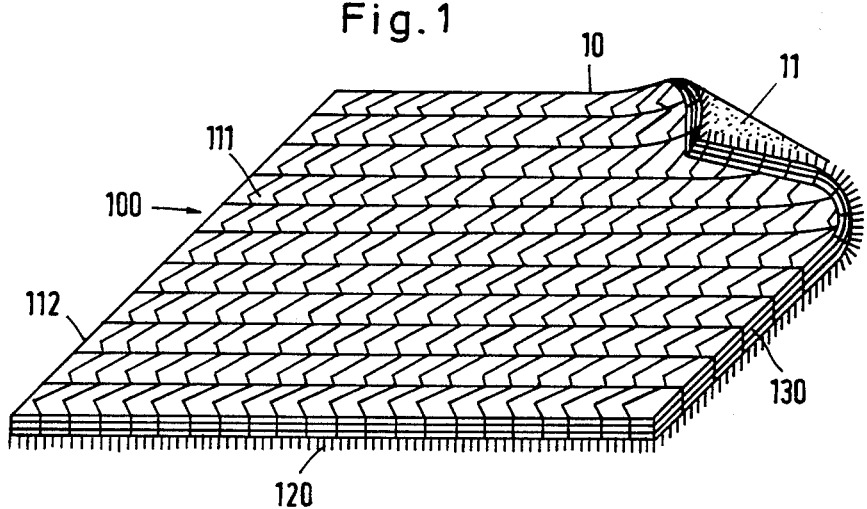
FIG. 1 is a diagrammatic view of part of the wound textile comprising a covering layer made from a completely synthetic, hydrophobic material and an absorbent layer of hydrophilic threads.

According to the embodiment of FIG. 1, the wound textile web 100 comprises a covering layer 111, made from completely synthetic, hydrophobic material, and an absorbent layer 130, which is formed by transversely joining, hydrophilic threads 112 and which is greatly roughened, as is indicated at 120.

Figure 2:
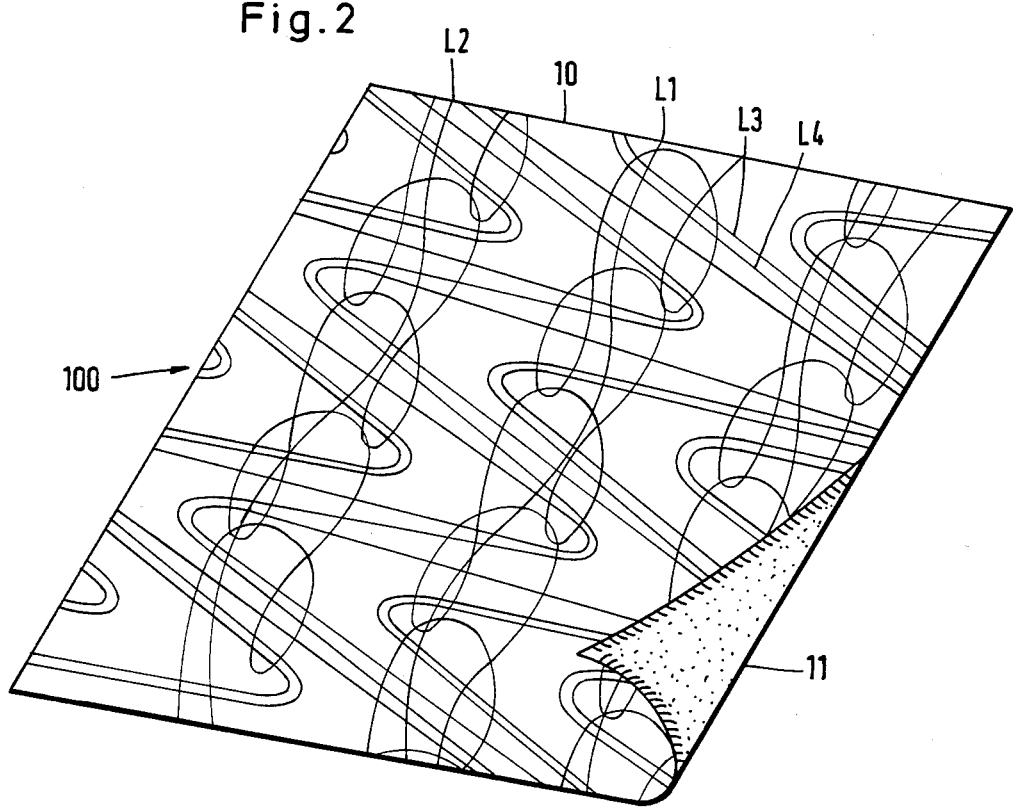
FIG. 2 is a diagrammatic view of part of the wound textile with the mesh-forming threads and the highly absorbent weft yarns incorporated into the fabric.

Side 10 of the completely synthetic material web 100 facing the wound is formed by mesh-forming threads of layer L1 made from polyester, polyamide, polypropylene or the like. The transversely joining hydrophilic threads of layers L2, L3 and L4 are formed from cotton, staple fibre or linen yarns, which are incorporated into the web as a weft. The wound-remote side 11 of the wound textile (FIG. 2) is roughened for increasing the pore volume of the absorbent layer. The completely synthetic threads of fold L1 are made resistant to separation by thermosetting.

What is claimed is:

1. A multiple-layer, woven, flat wound textile comprising:
   a smooth hydrophobic cover layer having an exposed surface adapted to face a wound without sticking thereto, being permeable to secretions from the wound, and including loops of synthetic, hydrophobic threads; and
   a roughened, hydrophilic second layer adapted to be separated from the wound by the cover layer, said second layer including a filling formed of hydrophilic threads for drawing secretions through the cover layer from the wound, the hydrophilic threads on the surface of the second layer opposite the cover layer exposed surface being roughened to increase the absorbency thereof.

2. A wound textile according to claim 1 wherein the synthetic hydrophobic threads are dyed with a blue, toxicologically unobjectionable dye.

3. A wound textile according to claim 1, wherein one or more of the hydrophilic threads are highly twisted.

4. A wound textile according to claim 1, wherein the synthetic, hydrophobic threads are made resistant to separation by thermosetting.

* * * * *